(12) United States Patent
Tchagang (10) Patent No.: US 8,396,872 B2
(45) Date of Patent: Mar. 12, 2013

(54) ORDER-PRESERVING CLUSTERING DATA ANALYSIS SYSTEM AND METHOD

(75) Inventor: Alain B. Tchagang, Ottawa (CA)

(73) Assignee: National Research Council of Canada, Ottawa, ON (CA)

( * ) Notice: Subject to any disclaimer, the term of this patent is extended or adjusted under 35 U.S.C. 154(b) by 119 days.

(21) Appl. No.: 13/107,288

(22) Filed: May 13, 2011

(65) Prior Publication Data

US 2011/0282876 A1   Nov. 17, 2011

Related U.S. Application Data

(60) Provisional application No. 61/334,740, filed on May 14, 2010.

(51) Int. Cl.
*G06F 7/00* (2006.01)

(52) U.S. Cl. .................................................... 707/737

(58) Field of Classification Search .................. 707/737, 707/736, 705; 702/176, 182, 189, 190, 167, 702/20
See application file for complete search history.

(56) References Cited

U.S. PATENT DOCUMENTS

| | | | |
|---|---|---|---|
| 5,806,064 A * | 9/1998 | Garza ................................... | 1/1 |
| 6,263,287 B1 | 7/2001 | Zheng et al. | |
| 6,876,930 B2 | 4/2005 | Murray et al. | |
| 6,965,831 B2 | 11/2005 | Domany et al. | |
| 6,996,476 B2 | 2/2006 | Najarian | |
| 7,010,430 B2 | 3/2006 | Nakashige et al. | |
| 7,031,844 B2 | 4/2006 | Bozinov et al. | |
| 7,031,847 B1 | 4/2006 | Nozaki et al. | |
| 7,043,500 B2 | 5/2006 | Leary | |
| 7,065,451 B2 * | 6/2006 | Garner et al. ................... | 702/20 |
| 7,127,354 B1 | 10/2006 | Nozaki et al. | |
| 7,174,344 B2 | 2/2007 | Campos et al. | |
| 7,257,562 B2 | 8/2007 | Farnet et al. | |
| 7,289,911 B1 | 10/2007 | Rigney | |
| 7,308,364 B2 | 12/2007 | Shaughnessy et al. | |
| 7,369,961 B2 * | 5/2008 | Castelli et al. ................ | 702/176 |
| 7,386,523 B2 | 6/2008 | Diao | |
| 7,565,346 B2 * | 7/2009 | Fan et al. .............................. | 1/1 |
| 2002/0052692 A1 | 5/2002 | Fahy | |
| 2002/0115070 A1 | 8/2002 | Tamayo et al. | |
| 2002/0169560 A1 | 11/2002 | Hytopoulos et al. | |
| 2003/0036071 A1 | 2/2003 | Lukashin | |

(Continued)

FOREIGN PATENT DOCUMENTS

| | | |
|---|---|---|
| WO | 0130973 | 5/2001 |
| WO | 0173602 | 10/2001 |

(Continued)

OTHER PUBLICATIONS

English Abstract of JP2008225689; published Sep. 25, 2008; Applicant Nat. Inst. of Agrobio. Sciences; Dainakomu KK.

(Continued)

*Primary Examiner* — Hung T Vy (74) *Attorney, Agent, or Firm* — Jason E J Davis (57) ABSTRACT

Clustering data analysis that is robust to noise and is able to extract the most reliable information from sequential data comprises the ranking all of the measurement values across a third dimension of a 3D dataset in a selected one of an increasing order or a decreasing order and producing a three dimensional array of ranked values therefrom. It further comprises identifying coherent 3D patterns from the 3D array of ranked values, and counting the number of identified coherent 3D patterns. Each coherent 3D pattern parameters with a similar ranking and across subsets of the set of elements to a same group defines a cluster.

19 Claims, 5 Drawing Sheets

U.S. PATENT DOCUMENTS

| | | | |
|---|---|---|---|
| 2003/0129660 | A1 | 7/2003 | Zien et al. |
| 2003/0212702 | A1 | 11/2003 | Campos et al. |
| 2003/0224344 | A1 | 12/2003 | Shamir et al. |
| 2004/0009489 | A1 | 1/2004 | Golub et al. |
| 2004/0077020 | A1 | 4/2004 | Mannick et al. |
| 2004/0101878 | A1 | 5/2004 | Jones |
| 2004/0128080 | A1 | 7/2004 | Tolley |
| 2004/0162679 | A1 | 8/2004 | Li |
| 2005/0027460 | A1 | 2/2005 | Kelkar et al. |
| 2005/0048535 | A1 | 3/2005 | Santin |
| 2005/0100929 | A1 | 5/2005 | Najarian |
| 2005/0130187 | A1 | 6/2005 | Shin et al. |
| 2005/0202421 | A1 | 9/2005 | Hirsch et al. |
| 2005/0240357 | A1 | 10/2005 | Minor |
| 2005/0240563 | A1 | 10/2005 | Domany et al. |
| 2006/0074566 | A1 | 4/2006 | Najarian |
| 2006/0078941 | A1 | 4/2006 | Santin |
| 2006/0084075 | A1 | 4/2006 | Ishiura et al. |
| 2006/0282916 | A1 | 12/2006 | Hibino |
| 2008/0027954 | A1 | 1/2008 | Gan et al. |
| 2010/0153400 | A1* | 6/2010 | Namir ................... 707/737 |

FOREIGN PATENT DOCUMENTS

| | | |
|---|---|---|
| WO | 02059367 | 8/2002 |
| WO | 03072701 | 9/2003 |

OTHER PUBLICATIONS

English Abstract of WO 2008102825; published Aug. 28, 2008; Applicant Articell System Corp.; Nakayama Yoichi.

Androulakis et al., "Analysis of Time-Series Gene Expression Data: Methods, Challenges and Opportunites", Annu. Rev. Biomed. Eng., 9:205-28, 2007.

Araujo et al., "ParTriCluster: A Scalable Parallel Algorithm for Gene Expression Analysis", Proceedings of the 18th International Symposium on Computer Architecture and High Performance Computing (SBAC-PAD'06), 2006.

Bar-Joseph et al., "Continuous Representations of Time-Series Gene Expression Data", Journal of Computational Biology, vol. 10(3-4), p. 341-356, 2003.

Ben-Dor et al., "Discovering Local Structure in Gene Expression Data: The Order-Preserving Submatrix Problem", RECOMB'02, Washington DC, p. 49-57, Apr. 18-21, 2002.

Cernetich et al., "Involvement of Gonadal Steroids and Gamma Interferon in Sex Differences in Response to Blood-Stage Malaria Infection", Infection and Immunity, vol. 74(6), p. 3190-3202, 2006.

Eulgem T., "Regulation of the Arabidopsis Defense Transcriptome", TRENDS in Plant Science, vol. 10(2), p. 71-78, 2005.

Famili et al., "Discovering Informative Genes from Gene Expression Data: A Multi-Strategy Approach", the 18th European Conference on Machine Learning, Warsaw Poland, Sep. 17-21, 2007.

Jiang et al., "gTRICLUSTER: A More General and Effective 3D Clustering Algorithm for Gene-Sample-Time Microarray Data", BioDM, LNBI 3916, p. 48-59, 2006.

Jiang et al., "Mining Coherent Gene Clusters from Gene-Sample-Time Microarray Data", in Proc. of the 10th ACM SIGKDD Conf. (KDD'04), 2004.

Johnson et al., "Salicylic Acid and NPR1 Induce the Recruitment of Trans-Activating TGA Factors to a Defense Gene Promoter in Arabidopsis", The Plant Cell, vol. 15, p. 1846-1858, 2003.

Madeira et al., "Biclustering Algorithms for Biological Data Analysis: A Survey", IEEE Transactions on Computational Biology and Bioinformatics, vol. 1(1), p. 24-45, 2004.

Phan et al., "A Novel Pattern Based Clustering Methodology for Time-Series Microarray Data", International Journal of Computer Mathematics, vol. 84(5), p. 585-597, 2007.

Pieterse et al., "NPR1: The Spider in the Web of Induced Resistance Signaling Pathways", Current Opinion in Plant Biology, vol. 7, p. 456-464, 2004.

Prelic et al., "A Systematic Comparison and Evaluation of Biclustering Methods for Gene Expression Data", Bioinformatics, vol. 22(9), p. 1122-1129, 2006.

Schliep et al., "Using Hidden Markov Models to Analyze Gene Expression Time Course Data", Bioinformatics, vol. 19, suppl. 1, p. i255-i263, 2003.

Tang et al., "Prediction of Co-Regulated Gene Groups Through Gene Ontology", Proceedings of the 2007 IEEE Symposium on Computational Intelligence in Bioinformatics and Computational Biology (CICBC 2007).

Tchagang et al., "DNA Microarray Date Analysis: A Novel Biclustering Algorithm Approach", EURASIP Journal on Applied Signal Processing, vol. 2006, article ID 59809, p. 1-12.

Tchagang et al., "GOAL: A Software Tool for Assessing Biological Significance of Genes Groups", BMC Bioinformatics, 11:229, 2010.

* cited by examiner

| GO terms | 1 | | 2 | | 3 | | 4 | | 5 | | 6 | |
|---|---|---|---|---|---|---|---|---|---|---|---|---|
| | % | p-value | % | p-value | % | p-value | % | p-value | % | p-value | % | p-value |
| cofactor metabolic process (GO:0051186) | 14 | 3.4E-12 | | | | | | | | | | |
| cellular metabolic process (GO:0044237) | 22 | 1.2E-08 | | | | | | | 22 | 4.5E-02 | | |
| cofactor biosynthetic process (GO:0051188) | 10 | 3.8E-08 | | | | | | | | | | |
| metabolic process (GO:0008152) | 30 | 1.4E-07 | | | | | | | | | | |
| negative regulation of biological process (GO:0048519) | | | | | 29 | 1.1E-02 | | | | | | |
| positive regulation of cellular process (GO:0048522) | | | 18 | 5.4E-04 | 21 | 3.1E-02 | | | | | | |
| protein metabolic process (GO:0019538) | | | | | 21 | 4.5E-02 | | | | | | |
| primary metabolic process (GO:0044238) | | | | | 21 | 5.0E-02 | | | | | | |
| electron transport chain (GO:0022900) | | | | | | | | | 16 | 2.3E-02 | | |
| DNA metabolic process (GO:0006259) | | | 26 | 9.4E-08 | | | | | 22 | 1.2E-02 | | |
| DNA replication (GO:0006260) | | | 21 | 9.5E-08 | | | | | 16 | 1.0E-02 | | |
| cell cycle (GO:0007049) | | | 18 | 7.7E-06 | | | | | 16 | 3.6E-02 | | |
| M phase (GO:0000279) | | | 13 | 1.9E-05 | | | | | | | | |
| DNA metabolic process (GO:0006259) | | | | | | | 16 | 3.9E-06 | | | | |
| DNA replication (GO:0006260) | | | | | | | 15 | 2.9E-06 | | | | |
| intracellular signaling pathway (GO:0023034) | | | | | | | | | | | | |
| intracellular signal transduction (GO:0035556) | | | | | | | | | | | | |
| phosphorylation (GO:0016310) | | | | | | | 18 | 3.4E-06 | | | | |
| phosphate metabolic process (GO:0006796) | | | | | | | 18 | 7.8E-06 | | | | |
| nucleocytoplasmic transport (GO:0006913) | | | | | | | | | | | 33 | 3.3E-02 |

FIG. 6

| GO term | IM | | IF | | GM | | GF | |
|---|---|---|---|---|---|---|---|---|
| | # | p-value | # | p-value | # | p-value | # | p-value |
| Apoptosis (GO:0006915) | 45 | 4.7e-15 | 40 | 3.3e-12 | 37 | 1.8e-10 | 37 | 7.2e-12 |
| Programmed cell death (GO:0012501) | 44 | 1.2e-12 | 40 | 1.5e-10 | 37 | 7.2e-09 | 36 | 1.2e-09 |
| Cell death (GO:0008219) | 43 | 2.2e-11 | 39 | 1.9e-09 | 37 | 2.4e-08 | 33 | 1.8e-07 |
| Immune response (GO:0006955) | 34 | 2.3e-15 | 38 | 5.4e-19 | 32 | 4.2e-14 | 28 | 2.8e-12 |
| Defence response (GO:0006957) | 47 | 5.3e-19 | 53 | 3.5e-24 | 51 | 1.3e-22 | 40 | 5.2e-16 |
| B-cell activation (GO:0042113) | 9 | 4.9e-05 | 10 | 6.1e-06 | 8 | 2.5e-04 | 7 | 6.9e-04 |
| T cell activation (GO:0046631) | 20 | 1.7e-13 | 22 | 8.0e-16 | 19 | 1.2e-12 | 16 | 2.0e-10 |

ORDER-PRESERVING CLUSTERING DATA ANALYSIS SYSTEM AND METHOD

FIELD OF THE INVENTION

The present invention relates in general to data analysis and data mining, and more specifically, it relates to a system and method for carrying out clustering data analysis based on order-preserving trends.

BACKGROUND OF THE INVENTION

There are many systems of data that require clustering data analysis, specifically clustering data that exhibits a same or similar trend. Some applications call for the clustering of aligned, relatively short, units of data (a sequence of 3-8 values). Often noise within the data is problematic, and increasingly greater volumes of data are analyzed. In general, an efficient and computationally inexpensive algorithm for trend-based clustering of similar data units is desired.

One such application for clustering data analysis comes from microarray technology, which has met with substantial commercial success over the past decade, in part because of its ability to quantify samples with high throughput. Thousands of genes can be examined concurrently under the same conditions. This allows for the identification of groups of co-expressed genes, which may be co-regulated. Genes exhibiting similar responses to triggers are more likely to be controlled by similar regulatory mechanisms. This is often referred to as the "guilt by association" principle [1]. Identifying coherent expression responses is important for identifying co-regulation and for understanding the underlying machinery driving the co-expression. One critical problem is to verify the common regulatory mechanism [1]. Therefore, a commonly repeated step in the analysis of gene expression is to identify those measured transcripts that appear to be correlated to each other. From a computational perspective, this is a clustering problem.

Clustering of co-expressed genes is an active data mining topic that has advanced in parallel with development of microarray technology. There is a vast literature on clustering algorithms developed for microarray data analysis [1-16]. Pioneering works in this area identify full space clusters, but, in many applications, subspace clusters are more meaningful [8]. Biclustering algorithms were recently proposed to find subgroups of genes that exhibit a same behavior across subsets of samples, experimental conditions, or time points [8-12]. Nowadays, it is possible to collect expression levels of a set of genes under a set of biological samples during a series of time points. Such data have three dimensions, gene-sample-time (GST), and thus are called 3D microarray gene expression data [13]. The full space clustering and biclustering concepts do not satisfactorily take advantage of the 3D data collected, and do not fully extract the biological information hidden within the GST data. Triclustering has been proposed to improve data mining of 3D microarray gene expression data.

The prior art recognizes the value for identifying order-preserving clusters as opposed to other trends that are not order-preserving. For example, [12] proposes a technique for identifying order-preserving submatrices (OPSMs) within an n-by-m matrix, where each row corresponds to a gene and each column to an experiment. Their method effectively produces an n-by-m rank matrix, in which the m values in each row are numbers from 1 . . . m. The (i. j) entry of the rank matrix is the rank of the readout of gene i in experiment j, out of the m readouts of this gene. Each row is therefore an example of an order-preserving abbreviated characterization of the m-vector of expression values. As is noted in [12], the OPSM problem is NP-complete. The identification of all of the columns for which some subset of the rows exhibit a trend that is order-preserving is computationally very expensive as the size of the matrix grows. Accordingly, [12] discloses a probabilistic model for uncovering a hidden OPSM with a reportedly "very high success rate".

A 3D cluster consists of a subset of genes that are coherent on a subset of samples along an interval of time-series. Coherent clusters may contain information used to identify phenotypes, associate genes with phenotypes, and identify expression rules. Triclustering was first introduced in [14], and a similar idea was mentioned in [13]. Pioneering works on triclustering algorithm relied on graph-based approaches to mine triclusters. Unfortunately, those methodologies introduce approximations in their design, and these approximations lead to risks that significant triclusters will be missed, especially when the 3D microarray gene expression data dealing with a short time series is used. For example, the algorithm described in [14] mines the maximal triclusters satisfying a constant multiplicative or additive relationship. Such a strict constraint considerably limits the capability of an algorithm to identify some useful patterns and may not be able to fully cope with noise when dealing with short time-series or even in general time-series gene expression data. The triclustering algorithms developed in [15-16] are equally problematic in this regard.

Applicant is aware of documents directed to methods and algorithms for analysis of microarray gene expression data, including: U.S. Pat. Nos. 6,965,831; 2005/0240357; 7,043,500; 2003/0129660; 2003/0224344; 2005/0240563; 2008/0027954; WO01/73602 U.S. Pat. No. 7,174,344; and U.S. Pat. No. 7,386,523. None of these deals with the identification of order preserving patterns, and none of them deals with the clustering of 3D short time-series gene expression data. US2003/0224344 uses probabilistic modeling of the data and graph theoretic techniques to identify subsets of genes that jointly respond across a subset of attributes. The clustering algorithms filed in U.S. Pat. Nos. 7,043,500; 7,043,500; 2003/0129660; 2003/0212702; 2005/0240357; 2005/0240563; 2008/0027954; 7,174,344; 7,386,523, and WO01/073602 are more similar to traditional clustering algorithms, that are very similar to the classical K-means clustering algorithm. Some of these (U.S. Pat. No. 7,174,344; and U.S. Pat. No. 7,386,523) do not appear to apply specifically to analysis of gene expression data.

A coupled two-way clustering (CTWC) algorithm is described in U.S. Pat. No. 2005/0240357 and U.S. Pat. No. 6,965,831. The CTWC algorithm defines a generic scheme for transforming a one-dimensional clustering algorithm into a bi-clustering or 2D clustering algorithm. It relies on having a one-dimensional traditional clustering algorithm that discovers significant clusters. Given such an algorithm, the coupled two-way clustering procedure recursively apply the one-dimensional algorithm to sub-matrices, aiming to find subsets of genes giving rise to significant clusters of attributes and subsets of attributes giving rise to significant subsets of genes.

There are also a number of prior art documents related to methods of analysis of gene expression data including data clustering as one of the processing steps. These documents include: U.S. Pat. Nos. 6,263,287; 6,876,930; 6,996,476; 7,010,430; 7,031,844; 7,031,847; 7,127,354; 7,289,911; 2002/0052692; 2002/0115070; 2002/0169560; 2003/0036071; 2004/0128080; 2005/0027460; 2005/10100929;

2005/0130187; 2006/0074566; 2006/0084075; WO 03/072701; WO 2006/087240; and WO 2008/102825.

There are also a number of documents related to applications of clustering of gene expression data. These documents illustrate various, mostly diagnostic, applications of gene clustering based on analysis of gene expression data, usually using DNA microarrays for measuring gene expression levels. These documents include: U.S. Pat. Nos. 7,257,562; 7,308,364; 2004/0009489; 2004/0077020; 2004/0101878; 2004/0162679; 2005/0048535; 2005/0202421; 2006/0078941; 2006/0282916; WO 01/30973; WO 02/059367; and JP 2008/225689.

However, there is still a need for a technique for data analysis, minimally affected by noise, that is able to cluster short sequences of (e.g. 3-20, more preferably 3-8) values according to a trend of the values.

SUMMARY OF THE INVENTION

The objective of the present invention is to provide an improved technique for clustering data analysis. The system and method according to the present invention identifies order preserving clusters. As is known in the art, two value sequences are part of a same order-preserving cluster only if they exhibit equivalent trends under any sequence reordering.

According to the present invention, there is provided a novel clustering data analysis technique, particularly suited for short time-series data mining of experimental genomic, proteomic, or materiomics, or other applications that involve clustering short sequences of values according to their trend, as the clustering data analysis technique is able to identify all clusters with coherent evolution from a given dataset. It can be extended to longer time-series datasets by recursion, for example with a windowing function or other partitioning of the data.

The clustering data analysis technique assigns an abbreviated order preserving characterization to each of the sequences of values to facilitate comparisons of large sets of data (e.g. more than a few thousand sets of data sequences to be trended), and removing an effect of noise. Unlike [12], which provides an abbreviated order preserving characterization to data from a variety of experiments, and then seeks to identify essentially random subsets of the experiments that are coherent, according to the present invention, only data that is part of a same experiment are treated this way. Whereas in [12] the expression values that are characterized by ranking, come from independently scaled gene expression values combined from different readouts for different experiments (tissues), which may be relative or absolute measures of expression level, the expression values characterized in accordance with the present invention are sequences of values that represent changes in observed values as a function of a variable, such as time, position within a tissue, temperature, concentration of a solute, electric or magnetic field, or other property or index of properties. The abbreviated order preserving characterization of such values is particularly advantageous because the difference between the expression values from a single experiment is more reliable a measure (when noise is evident) than the values themselves, especially when the values are well quantified. Thus, in comparison with [12], the present invention uses value sequences that represent changes in observed values as a function of a variable, provides a more flexible and effective analysis, has a complexity that is linear, and thus is computationally feasible on larger datasets, is optimal, for a given quantification, as it does not rely on probabilistic clustering methods, and further provides greater possibilities for analysis by providing a complete classification of the sequences of variables. These substantial advantages are provided by limiting the search from all subsets of all experimental values to patterns of short sequences (3-20, more preferably 3-8, values), which are considered indivisible by the analysis, and treating different samples and genes independently.

Accordingly, a data clustering method performed with an electronic processor is provided, the method comprising: providing access to a dataset, computing an order preserving abbreviated characterization of each of the value sequences, and associating value sequences characterized the same to respective clusters by annotating a record containing the value sequence to identify the characterization, and/or by adding an identifier of the associated value sequence to a record created for the class. The dataset is stored electronically in a dataset structure on a memory, and includes at least a few thousand aligned sequences in at least one set. Each sequence has a same number (B) values, where $3 \leq B \leq 20$, and more preferably $3 \leq B \leq 8$. In our examples, $3 \leq B \leq 4$. The value sequences represent changes in observed values as a function of a variable, and the changes are subject to noise. The order preserving abbreviated characterization is such that two value sequences will only have the same abbreviated characterization if they exhibit equivalent trends under any sequence reordering. Computing the order preserving characterization may comprises generating a rank sequence in which each of the values in the sequence is replaced with its corresponding rank in the sequence, in either an increasing order or a decreasing order.

The dataset may be in a form of a three-dimensional array of values with the first dimension being associated with a set of parameters, and the second dimension being associated with a set of elements, where each of the value sequences represents the function of the variable associated with a given parameter under a given element. And so, the method may further comprise regrouping one or more collections of associated parameters, each collection having parameters from a respective set of the sequences, and identifying a set of elements, over which the collection of associated parameters are clustered. For example, the collection of associated parameters may be a same nominal parameter. The method may further identify parameters that are clustered the same throughout all sets, or co-clustered in different clusters in different sets, or may identify parameters that have order preserving concentrations over some but not all of the sets. For example, the method may involve receiving an identification of one or more of the sets, and associating all value sequences, or parameters of sets of sequences, characterized the same within the identified sets.

More specifically, the dataset may be in a form of a three-dimensional array of values with the first dimension being associated with a set of constituents, and the second dimension being associated with a set of samples, where each of the value sequences represents the concentration of a given constituent, such as a gene, within the given sample as a function of the variable, which may be time.

The method may extract multiple sequences of B values from respective longer value sequences. The method may comprise iterating the computation of the order preserving abbreviated characterization for each of a plurality of the extracted sequences of B values, and associating two of the longer value sequences with a respective cluster if corresponding ones of the plurality of extracted sequences of B values of the two longer value sequences match.

The method may further comprise performing statistical significance analysis on each identified order preserving cluster, for example by computing a tail probability that a random data set will contain an order preserving cluster. The method may further comprise pre-processing all of the values through data smoothing and quantification, prior to computing the order preserving characterization. The method may further comprise performing a biological evaluation of each of the identified order preserving clusters, by computing a Fisher's exact test on a 2×2 contingency table to produce a plurality of values corresponding to a significance of gene ontology enrichment in a given order preserving cluster.

Also accordingly, a system for analysing data is provided, the system comprising memory for storing a dataset structure containing an electronically accessible dataset, the dataset having at least one set of S aligned sequences of B values, where the value sequences represent changes in observed values as a function of a variable subject to noise, and $3 \leq B \leq 20$; and an electronic processor configured to access the dataset, having program instructions for: computing an order preserving abbreviated characterization of each of the value sequences, such that two value sequences will have the same abbreviated characterization only if they exhibit equivalent trends under any sequence reordering; and associating value sequences characterized the same to respective clusters by annotating a record containing the value sequence to identify the characterization, and/or by adding an identifier of the associated value sequence to a record created for the class.

The dataset may be as characterized above with respect to the method.

The electronic processor may be configured to operate a series of modules, including: a ranking module adapted to rank all of the measurement values across a third dimension of the array in a selected one of an increasing order or a decreasing order and producing a 3D array of ranked values therefrom; a pattern identification module adapted to identify coherent 3D patterns in the 3D array of ranked values and counting the number of identified coherent 3D patterns; and an assignment module adapted to, for each said identified coherent three dimensional pattern, assign parameters with a similar ranking along the third dimension and across subsets of the set of elements to a same group, thereby identifying order preserving clusters.

Furthermore, a computer program product is provided, the product comprising a computer-readable storage medium storing a comprising computer program instructions that, when executed by a processor, implement the method of clustering data analysis of claim 1.

Moreover, a data clustering method is provided to be performed with an electronic processor. The data clustering method comprising: providing access to an experimental genomic, proteomic, or materiomic dataset stored electronically in a dataset structure on a memory, the dataset having at least a few thousand aligned short time series sequences, each sequence associated with a respective sample, and a respective gene, protein, or material component, and comprised of a sequence of 3 to 20 values, each of the values in the sequence representing an observed measurement of the associated component within the associated sample at a respective experimental condition associated with the position of the value in the sequence; computing an order preserving abbreviated characterization of each of the value sequences, such that two value sequences will only have the same characterization if they exhibit equivalent trends under any sequence reordering; and associating value sequences characterized the same to respective clusters by annotating a record containing the value sequence to identify the characterization, and/or by adding an identifier of the associated value sequence, component, sample or experimental condition to a record created for the class.

BRIEF DESCRIPTION OF THE DRAWINGS

These and other objects and advantages of the invention will become apparent upon reading the detailed description, provided merely by way of non-limitative examples, and upon referring to the drawings in which.

DETAILED DESCRIPTION OF PREFERRED EMBODIMENTS

A technique for clustering a dataset including a plurality of sequences of 3-20, more preferably 3-8 values to identify clusters of trends in the values, where the clusters are order-preserving, and provides a complete listing of the clusters without recourse to probabilistic methods.

Figure 1:
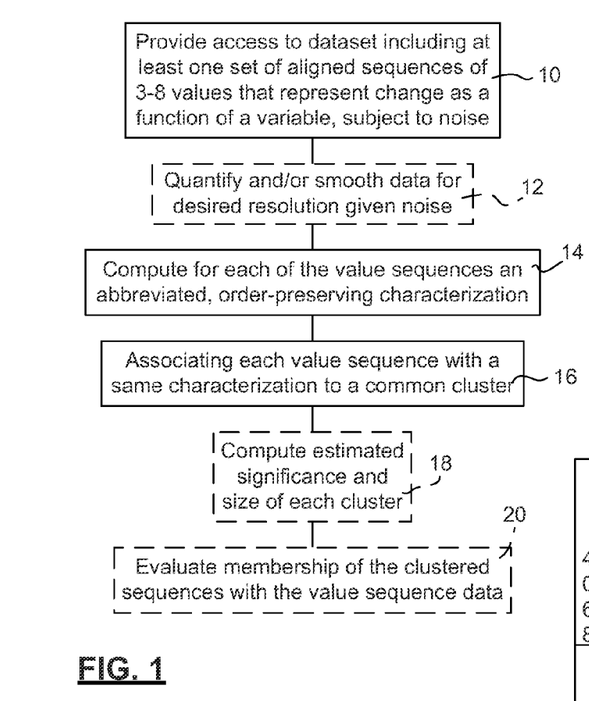
FIG. 1 is a block diagram illustrating the steps executed by the system and method in accordance with a preferred embodiment of the present invention.

FIG. 1 is a block diagram of principal steps of a method of clustering data analysis. In step 10, access is provided to a suitable dataset. The dataset includes a large number of aligned sequences, in at least one set, each sequence having 3-20 (more preferably 3-8) values that are measured from a common experiment under varying conditions. The values are observed as a function of a variable or index of variables, which may be time, such as the order in which measurements were taken. The one or more sets may each have a different number of sequences, although each set may be associated with the respective parameters which may overlap strongly with parameters of other sets. Each sequence has a same number of values. Typically each set would have several hundred to several tens of thousands of sequences or more. The dataset is electronically available, stored electronically in a dataset structure on a memory. For example, the dataset may be a 3D microarray of gene/protein/material expression (or like) data from experimental genomic, proteomic, or materiomic arts; each sequence associated with a respective sample, and a respective gene, protein, or material component, in which each of the values in the sequence represents an observed measurement of the associated component within the associated sample at a respective experimental condition that is associated with the position of the value in the sequence. Thus the dataset can be provided with a first dimension of the 3D array associated with a set of parameters, such as a set of components, a second dimension of the 3D array is associated with a set of samples, and a third dimension that identifies experimental conditions. Each of the values represents an observation associated with a parameter under an element, such as a concentration or other feature of the constituent within the sample as a function of the variable. The objective of the analysis is to identify the value sequences (i.e. the parameters, constituents, materials, genes, proteins, etc.) that have the same trend (i.e. sufficiently similar behaviour) under the variable, for different experiments (elements, samples, conditions).

Optionally, in step 12, the data is pre-processed. Several steps of pre-processing may be desirable depending on the data. To pre-process gene expression data, smoothing and quantification are typically performed. Anomalous readings are typically discarded, on many experimental datasets. Some data pre-processing is geared to remove noise, including many data smoothing techniques [9-10]. DNA experimental data is known to contain missing values. Many techniques to recover missing values have been developed in the literature, for example, [9-10]. Of particular importance for the present invention is quantification. If data is taken from digitized real value signals, the values may have many decimal places more than the precision of the measurement. Still, comparisons between the values may accurately distinguish between values that have differences below the threshold of precision. Accordingly, choosing a granularity of the data points is of particular importance, in methods that make a stark distinction between equal values and non-equal values, as is done in the illustrated examples of an abbreviated order-preserving characterization.

For each value sequence, in step 14, an electronic processor performing the clustering data analysis computes an abbreviated order-preserving characterization for each sequence. To be order-preserving, the characterization should only treat two value sequences as being equivalent if they exhibit a same trend, regardless of the ordering of the sequences; i.e. a necessary condition for two sequences $s_1$ and $s_2$ to be given a same characterization, is that they exhibit the same trend on any reordering of the values in both sequences. So if there is a reordering of the values for which $s_1$ and $s_2$ do not have a same trend, they cannot be given a same characterization. For example, if we take these six three value sequences {A(1 2 3), B(2 5 7), C(1 6 2), D(2 6 0), E(1 2 7), F(1 0 1)}, one can see that for A,B,E the trend (at a simplest level of description) is upwards and upwards, while for C,D the trend is upwards followed by downwards, and F goes down and up. However, unlike A,B,E,C,D are not sufficiently similar to be of the same order preserving class, as switching the order of the $2^{nd}$ and $3^{rd}$ values, one sees that C*(126) goes up and up, while D*(206) goes down and then up. Representing each value in the sequence by its rank within the sequence produces a rank sequence of the value sequences (in our example, {A(1 2 3) B(1 2 3)C(1 3 2)D(2 3 1)E(1 2 3)F(2 1 2)}. The rank sequence provides a characterization that makes immediately clear to which class the sequence belongs, at this level of description of the trend. The characterization is abbreviating in that the number of bits required to represent an arbitrary value sequence as a rank sequence is less than the number of bits required to represent the value sequence. While the values in this toy example range over the integers (and typically observed values range over "reals"), the rank matrix has only values between 1 and 3. The rank sequence is a preferred example of an abbreviated order-preserving characterization of the value sequence.

The order-preserving characterization may be more refined than the ranking sequence, and thus order-preservation is a necessary, but may not be a sufficient condition for the characterization. For example, if it is desired to differentiate value sequences like E, from those of A,B, another term may be added to the characterization to indicate how (comparatively) uniform the rising or falling is at the two steps. While A,B have substantially uniform step size, the second step in F is markedly greater than the first. To compute the rank sequence, differences between the values are computed, and so these can be used to add further constraints without appreciably increasing complexity of the algorithm. In the examples below, the ranking is a necessary and sufficient condition for two sequences to be characterized the same.

After each value sequence is characterized, the value sequence, or the parameter associated with it under the element, is assigned a class uniquely associated with the order-preserving abbreviating characterization that it receives. This may be accomplished by annotating a record containing the value sequence, and/or by adding an identifier of the associated value sequence (or component, sample, and experimental condition) to a record created for the class. Thus in step 16, a value sequence, or the parameters they represent, are classified. Once the classification is complete, each value sequence/associated parameter, is associated with a respective class. To the extent that the same nominal parameters are present in each set of sequences, regrouping of these parameters within a common class may be important for determining a degree to which the parameters themselves, as opposed to occurrences of the parameter in a specific element, are correlated with each other. While the same nominal parameters associations are compelling, other associations between the parameters or other groupings of the elements within the one or more sets can equally be suggested by the data analyzed, and a multiplicity of associations may be examined. When the parameters are associated nominally (by name), then the cluster is referred to as a tricluster, where the same gene, protein, material (or other parameter) is associated with the same trend over the same set of conditions within one or more tissues or samples. As a certain fraction of any two parameters would be expected to be correlated by random chance, larger groups of similar parameters that are associated with the same classes over a same subset of the tissues or samples may be important for distinguishing happenstance correlation from an underlying association. Thus when a substantial fraction of the sequences of two parameters are found to be in the same classes within several or many elements, the parameters themselves may be said to be classified over the range of elements.

One advantage of the present, complete, classification is the flexibility with which the parameters can be analysed. While classification in a same category over the elements is one important notion, referred to as coexpression in biological sciences, there are other ways that parameters may be linked. For example, if parameters exhibit opposite tendencies (up up:down down, up same:down same, down up:up down, etc.) this could signify that there is a competition or negative correlation between the parameters. Furthermore, assessing the element overlap between parameters that are the most highly clustered (i.e. clustered over the greatest numbers of elements) can be important for determining different relationships between the parameters, such as a phase lag (e.g. up, up, down, down, same, same: same, same, up, up, down, down), or otherwise. Furthermore overlap of parameters over elements with respect to groupings of associated classifications can be readily performed, to assess other relationships between the parameters.

The invention may further comprise steps 18 or 20. A statistical analysis of the significance of each cluster may be computed to assess the likelihood that the cluster is mere happenstance (in a variety of ways known in the art), and experimental evaluation of each cluster may be computed. In cases where the method is applied for analyzing gene expression data, the evaluation may be computed using a Fisher's exact test on a 2×2 contingency table to produce a plurality of values corresponding to a significance of gene ontology enrichment in a given cluster. Once the ranked sequences are classified, the value sequences themselves may be compared to identify more subtle cluster candidates that are degenerate in the characterization of the trend, and with the finer characterization, the process may be repeated to provide a new clustering of the data.

The method of FIG. 1 is preferably performed by a system for data clustering analysis, the system including an electronically accessible memory for storing the dataset, and an electronic processor configured to access the dataset. The electronic processor has program instructions for computing an order preserving abbreviated characterization of each of the value sequences, and associating value sequences characterized the same to respective clusters. For example, the program instructions may include: a ranking module adapted to rank all of the observed sequence values in a selected one of an increasing order or a decreasing order, to produce an array of ranked values; a pattern identification module adapted to identify coherent patterns in the array of ranked values, and counting the number of identified coherent patterns; and an assignment module adapted to, for each said identified coherent pattern, assign parameters with a similar ranking to a same group, thereby identifying order preserving triclusters.

The method of FIG. 1 can be provided as a computer program product having a computer-readable storage medium with computer program instructions that, when executed by a processor, implement the method of clustering data analysis. The computer program instruction may further perform statistical significance analysis on each said identified clusters. Preferably, the statistical significance is assessed by computing a tail probability that a random data set will contain a cluster.

EXAMPLES

An example of the present invention is provided for use in gene-sample-time, short time series datasets. A 3D microarray gene expression dataset or gene-sample-time (GST) microarray dataset is a real-valued N×M×L matrix is provided, representing set of N genes G={$g_1, \ldots g_n, \ldots g_N$}, a set of M biological samples S={$s_1, \ldots, s_m, \ldots, s_M$}, and a series of L time points T={$t_1, \ldots, t_l, \ldots, t_L$}. Typically $10^{10} > N > 10^4$, $10 > M > 1$, and $20 > L > 3$. Each cell $a_{nml}$ in the matrix derives from an observed measurement of expression level of gene $g_n$ in sample $s_m$ at time (or under the conditions associated with) $t_l$. This 3D microarray dataset is referred to as: A=(G, S, T). The expression level of gene $g_n$ in sample $s_m$ across the time points (sequence) is denoted: $f_{nm}(t)$, which is a row vector. The expression level of a gene $g_n$ in all the samples, across all time points $f_n(s,t)$, is another name for the matrix A. Thus the 3D gene expression matrix can be viewed as a set of 2D matrices.

A 3D cluster or tricluster is a 3D submatrix C={$c_{ijk}$} of A (or $A_Q$—see below), or C={I, J, K}, with $I \subset G$, $J \subset S$, and $K \subset T$ (for a short time series experiment, K may necessarily be $\overline{T}$), such that the content of C={$c_{ijk}$: i∈I, j∈J, and k∈K}, verifies a desired pattern: that is, the cells $c_{ijk}$ of C are populated with values that have a same trend as each other, regardless of ordering patterns. An order preserving clustering associates the functions $f_{nm}(t)$ (the sequences), that are similar in that a sign of a difference between successive time points $k_{i+1} - k_i$ (being +, −, or 0), is the same for each i, and furthermore that the same holds for any permutation of the time points k. This measure of coherence simplifies the data sufficiently to facilitate computation, while capturing information important for identifying clusters. Once clusters have been identified, they are analyzed statistically, or to identify relations between the gene expressions.

Applicant's software takes a matrix A and a quantification threshold δ, and finds all triclusters C={I, J, K}, with at least $I_{min}$ genes, and at least $J_{min}$ samples, such that the content of each cluster is order preserving over all time points of the short time-series data. The triclustering process finds patterns that increase, decrease, or stay constant coherently between each pair of time points across the entire time series. After data preprocessing and normalization, the triclustering process has five main steps: 1) gene expression data quantification, 2) ranking of the value sequences, 3) identification of distinct patterns, 4) clustering the genes and/or samples having the same patterns, and 5) evaluation of the clusters.

The first step of the exemplary triclustering method, which is in fact optional (if δ is set to 0), involves quantification of the dataset. Smoothing, discarding of anomalous readings, impute the "missing" values, and other corrective measures are assumed to have taken place on the dataset used [9-10]. Choosing from among the various preprocessing techniques available is within the purview of those skilled in the art.

The triclustering method uses the following approach for data quantification. Given an input threshold δ, for each gene n and sample m, the method computes Q, a range of the function $f_{nm}(t)$ divided by δ (i.e. Q=$[(b_L - b_0)/\delta]$ where $b_0$=min ($f_{nm}(t)$), and $b_L$=max($f_{nm}(t)$), and δ>0). Then the interval [$b_0$ $b_L$] is divided into the ceiling of Q equal bins: [$b_0$ $b_1$] U . . . U [$b_{l-1}$ $b_l$] U . . . U [$b_{L-1}$ $b_L$], with $b_l = b_0 + l\delta$. As any outliers have been removed, these bin intervals will have mean populations reasonably well controlled by selection of δ. Quantified expression levels $q_l$ of the corresponding time points for the gene and sample are then limited to a centre value of one of these bins (i.e. $q_l = (b_{l-1} + b_l)/2$). Specifically, if the expression level $f_{nml}$ falls in the interval [$b_{l-1}$ $b_l$], then it is quantized to $q_l$. In general, the smaller δ, the greater the number of bins into which the data is divided, and the more information is retained. Logically δ is bounded below by a number that actually creates more bins than the number of values the can take, and above by a number that is larger than the expected range (which will likely collapse all values to a single bin). In practice, δ is typically chosen to vary from $1/10^{th}$ to $1/10,000^{th}$ of the expected range. Furthermore δ may be chosen to provide a fixed (e.g. 5-15%) number of distinct values that are binned together. Empirical approaches to determining δ may be preferred for any given data set, and several iterations of data analysis were performed with different δ values in Applicant's investigations. The matrix A with each value $a_{nml}$ replaced with its quantification value $q_l$ is the quantified 3D gene expression matrix $A_Q$.

The triclustering process uses the $A_Q$ to generate a 3D rank expression matrix R. The 3D rank expression matrix is an N×M×L matrix, R=[$r_n(s,t)$]=[$r_{nml}$], in which every $r_{nm}(t)$ is a vector of the ranks of the corresponding expression values in $f_{nm}(t)$, in increasing or decreasing order. For example, if the expression levels of gene $g_n$ in sample $s_m$ along the time-dimension is [1.5, 3, 0.5] then, the corresponding row in the rank matrix would be [2, 3, 1]. Note that, if more than two entries have the same value, they are given the same ranking. For example [0.5, 3, 0.5] would be [1, 2, 1]. The frequency of same values within the matrix is influenced by quantification.

There are several advantages associated with this transformation. The rank matrix R is populated with small ordinal values compared with the floating point values in Q. This expedites comparisons. The noise is significantly reduced, but the ordinal information provides reliable information for clustering purposes. As the data is simplified, clusters can be computed without the use of greedy algorithms, or probabilistic approaches, typically used to mine data in an unsupervised manner, and the clustering method is not biased like supervised approaches, where the clusters are of a prescribed pattern. Finally by ranking the data, exhaustive permutations along the time-dimension can be avoided while still obtaining all and only the order preserving patterns, reducing computation time. For any two rows $f_{nm}(t)$ of the same ranking $r_{nm}(t)$, under any permutation of the time points, their order is always preserved. The approach further allows for the identification of constant patterns, which are particular classes of order preserving clusters.

In its third step, the triclustering process identifies the set of distinct 3D coherent patterns found in $A_Q$ (or A if $\delta=0$). A sample space $\Omega$ is the set of all possible (non-empty) combinations of the samples, and $\Gamma$ is their number ($\Gamma=2^{|S|}-1$). So if $S=\{s_1 \, s_2\}$, then $\Omega=\{\{s_1,s_2\}, \{s_1\}, \{s_2\}\}$ and $\Gamma=3$. For each combination $\Omega_i \epsilon \Omega$, the exact number $h_i$ of distinct 3D order preserving triclusters that are found in the 3D dataset is the number of distinct 2D $r_n(\Omega_i,t)$ matrices of its corresponding 3D ranked matrix R. Thus, the set of distinct order preserving patterns, U, can be identified by considering R as a set of 2D matrices $r_n(\Omega_i,t)$ (i.e. $R=\{r_1(\Omega_i,t), r_2(\Omega_i,t), \ldots, r_n(\Omega_i,t), \ldots, r_N(\Omega_i,t)\}$ and identifying distinct $r_n(\Omega_i,t)$ in each. From the above definitions, one can easily show that the exact number $h_i$ of order preserving triclusters in the 3D gene expression matrix is the summation of $h_i$ over all i, while $h_i$ is the number of distinct 2D $r_n(\Omega,t)$ (rank matrices) corresponding to each $\Omega_i \epsilon \Omega$ as defined above.

Once the exact number of distinct 3D order preserving patterns has been identified, for each $Q_i \epsilon \Omega$, genes are assigned to one of the $h_i$ groups by comparing each distinct pattern $U_k$ of U to $r_n(\Omega_i,t)$, and assigning a gene n to the tricluster $C\{k\}$ when $U_k=r_n(\Omega_i,t)$. This approach is guaranteed to identify all order preserving triclusters of size I×J×K, with $I_{min} \leq I \leq M$, and $J_{min} \leq J \leq M$, and K=L, where $I_{min}$ and $J_{min}$ are the minimum number of genes and samples in a tricluster.

Divergent Pattern Identification

The procedure as presented above identifies sets of genes that behave similarly across the subsets of samples considered. These sets are interesting themselves, in that only genes with conserved trends across the sets are represented, removing much of the data, and permitting a researcher to focus more directly and quickly on the relevant genes. Some of the relevant genes are identified by other analyses.

If a set of genes are in a cluster over samples $s_1 \, s_2$, then at least those genes are in the cluster over samples $s_1$, as well as the cluster over samples $s_2$. But the set of genes having the same trend over samples $s_1 \, s_2 \, s_3$ is a subset of that set of genes. It is frequently of interest to understand what sample sets differentiate gene expression, as well as what genes are co-expressed in some sample conditions, and differently expressed in others.

The sets of divergent patterns D can be easily derived from the sets of conserved ones using the following approach: $D_{kl}=C\{k\}-C\{l\}=\{\{I_k-I_l\},\{J_k-J_l\}\}$, where $C\{k\}$ and $C\{l\}$ are two conserved triclusters with same ranking patterns. Basically, the above approach identifies sets of genes that are co-expressed in the subset of sample in $C\{k\}$, but split and express different trends in the identified samples. For example, if clusters $C\{k\}$ and $C\{l\}$ have the same trend, and if $C\{k\}=\{\{g_1,g_2,g_3,g_4\}, \{s_1,s_2\}, \{t_1,t_2,t_3\}\}$ and $C\{l\}=\{\{g_1,g_2\}, \{s_1,s_2,s_3\}, \{t_1,t_2,t_3\}\}$, then $D_{kl}=\{\{g_3,g_4\}, \{s_3\}, \{t_1,t_2,t_3\}\}$, meaning that genes $\{g_3,g_4\}$ have different behaviour in $\{s_3\}$ compared to $\{s_1,s_2\}$. The computational burden of this step is reduced because only triclusters with same ranking patterns (trend) are compared.

Statistical Significance

The statistical significance of each identified tricluster with at least $I_{min}$ genes and $J_{min}$ samples can be assessed by computing the tail probability that a random dataset of size N×M×L will contain an order preserving tricluster with $I_{min}$ or more genes and $J_{min}$ or more samples in it. In principle, the probabilistic description of a reference random matrix would be that of the observed noise in the microarray experiment [9, 12]. Since this distribution is difficult to calculate in closed form, an upper bound of this tail probability was estimated using the approach described in [9, 12].

Cluster Evaluation

The significance of gene ontology (GO) enrichment in a given tricluster can be computed using the Fisher's exact test on a 2×2 contingency table. The p-value of this test is calculated using the hypergeometric distribution, in accordance with the present examples.

Complexity Analysis

The overall complexity of the triclustering algorithm is $O(N\Gamma\Lambda)$. Recall that the 3D short time-series gene expression data A is an N×M×L matrix. The 3D rank matrix can be identified within $O(NML)$ time. The set of distinct 3D patterns can be identified with $O(N\Gamma)$. Finally, the set of coherent conserved triclusters can be identified within $O(N\Gamma\Lambda)$. In all, the complexity of the triclustering algorithm is $O(NML)+O(N\Gamma)+O(N\Gamma\Lambda)$, which is $O(N(ML+\Gamma+\Gamma\Lambda))$. Since $\Gamma\Lambda>\Gamma$ and $\Gamma\Lambda>ML$, the overall time complexity is $O(N\Gamma\Lambda)$. Note that the complexity for identifying the sets of divergent patterns from convergent ones is negligible.

Robustness to Noise

To test the robustness of the method to noise, we used the adjusted rand index (ARI). ARI has previously been used by several authors [4,16] for clustering techniques comparison and robustness to noise. ARI values lie between 0 and 1, and larger ARI values indicate more similarity between the clustering results. If the experimental result is perfectly consistent with the domain knowledge, the index value will be 1. If a clustering is no more than a random choice, the index will be zero.

Figure 2:
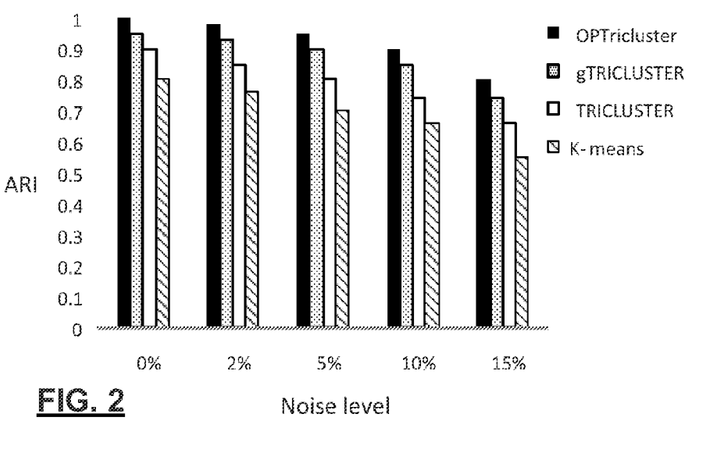
FIG. 2 is a graph illustrating robustness to noise and comparative analysis of the novel triclustering approach to the modified gTRICLUSTER, TRICLUSTER, and K means algorithms.

A simulated 3D microarray dataset with N=1000 genes, M=4 samples, and L=3 time points was generated, with four order preserving triclusters across the entire sample imbedded in the data. Thus the domain knowledge Y corresponds to the four embedded triclusters. We added 0%, 1%, 2%, 5%, and 10% noise into the original dataset and computed the ARI values between the triclustering results and the domain knowledge. For comparison, clustering was performed using the method of the present invention, versions of TRICLUSTER [14], gTRISCLUSTER [16] modified to deal with short time series, and K means clustering. The results are illustrated in FIG. 2.

It can be seen that the ARI values of the present invention (identified as OPTriCluster) are larger than that of gTRICLUSTER, TRICLUSTER, and K means clustering, indicating that the novel triclustering algorithm of present invention is more robust to noise than the prior art methods, regardless of tested level of noise added to the data.

Biological Application 1

Figure 3:
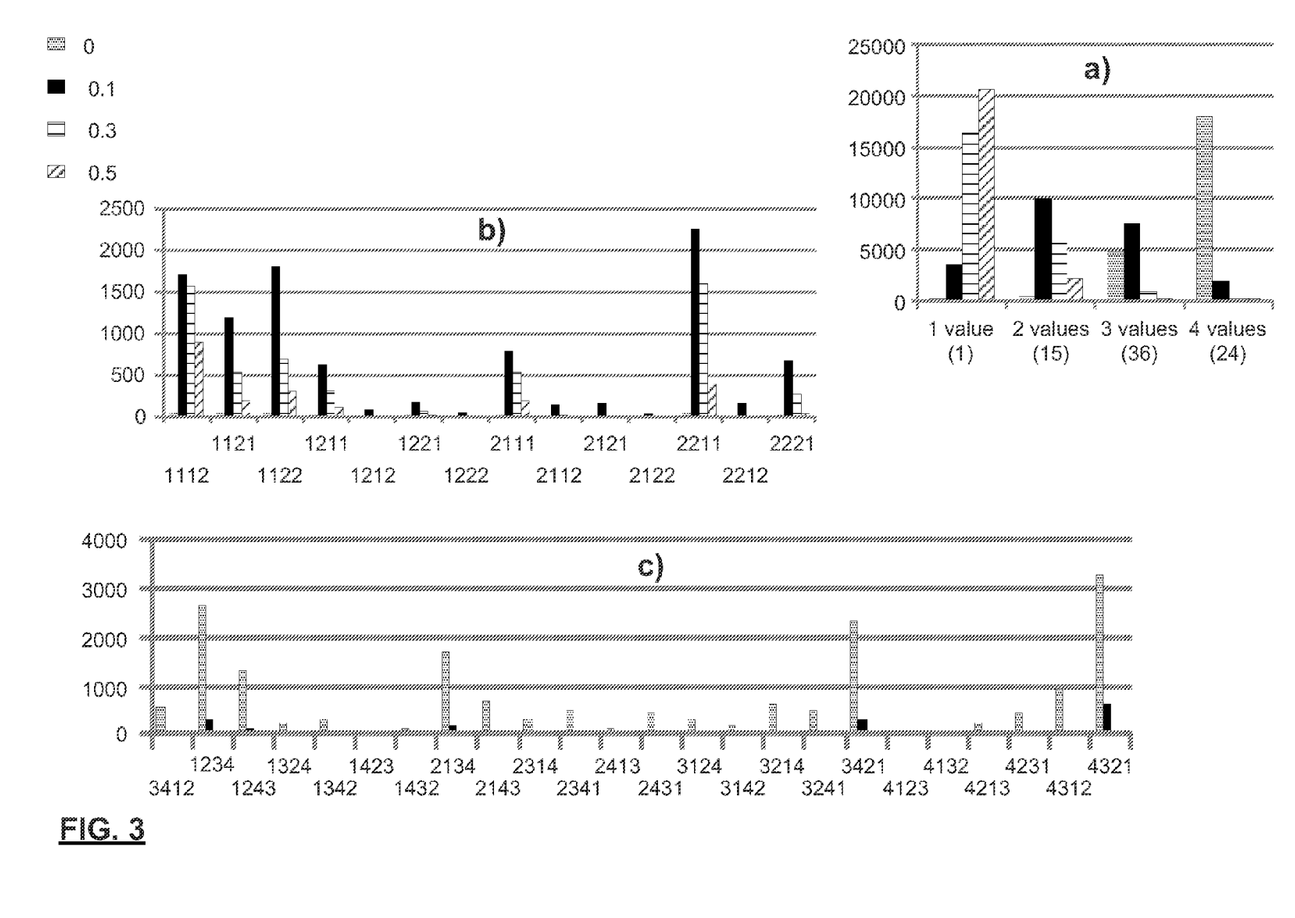
FIG. 3 includes three bar charts showing cluster statistics for 4 groups of the ranking orders as a function of 4 threshold ($\delta$) values, and distributions of the 4 threshold values within individual ranking orders for the $2^{nd}$ and $4^{th}$ groups.

FIG. 3a) is a bar chart of partitions of abbreviated characterizations (ranking orders) of short time-series (4-value) sequences under 4 different thresholds ($\delta=0, 0.1, 0.3, 0.5$), respectively for each value sequence. The distributions of the same dataset with 4 different thresholds is defined with respect to a partition of the set of sequence ranking orders.

Specifically, all ranking orders that has only one value (i.e. 1111) are in the first (1 value) partition, all ranking orders that have only two values (1112, . . . , 2211, . . . 2221) are in the second (2 values) partition, etc. FIGS. 3b),c) show the distributions of the dataset under the 4 quantification thresholds, in the second and fourth partitions, respectively. It will be noted that the larger the δ value, the fewer bins, and the wider the bins are (relative to the range of the value sequence), and the more sequences are clustered with fewer values, as the greater number of values are assigned to a same bin. Thus for δ=0, a bulk of the sequences are assigned to the 4 values partition, and conversely for δ=0.5, the bulk of the sequences are assigned to the 1 value partition. Typically δ is chosen having regard to an estimation of noise within the data.

The dataset used [20] comes from an experiment studying immune responses in mice infected by malaria (*Plasmodium chabaudi*), as a function of sex, and how this response is altered by the presence of gonadal steroids. A 3D short time-series gene expression dataset was downloaded from the Gene Expression Omnibus website [21], (accession number: GSE4324). This dataset has N=33,935 probes, represents two disease states (infected and non infected), two genders (male and female), two protocols (intact and gonadectomized), and experiments at four time points: 0, 3, 7, and 14 days after inoculation (DAI). The four biological samples used in this study are referred to as: intact male ($I_M$), intact female ($I_F$), gonadectomized male ($G_M$), and gonadectomized female ($G_F$).

After data pre-processing and normalization, 5783 significant probes corresponding to 5063 unique genes were retained for the experiment. The three dimensions of the data are: G (N=5783 probes), S (M=4 samples: $I_M$, $I_F$, $G_M$, and $G_F$), and T (L=4 time points: 0, 3, 7, and 14 DAI). The OPTriCluster parameters were set to: minimum number of genes in a cluster: $I_m$=1, minimum number of samples in a cluster $J_m$=1 and differential expression threshold δ=0.31. The algorithm generated clusters for each of $2^4-1$=15 subsets of samples: namely $\Omega$={{$I_M$, $I_F$, $G_M$, $G_F$}, {$I_M$, $I_F$, $G_M$}, {$I_M$, $I_F$, $G_F$}, {$I_M$, $G_M$, $G_F$}, {$I_F$, $G_M$, $G_F$}, {$I_M$, $I_F$}, {$I_M$, $G_M$}, {$I_M$, $G_F$}, {$I_F$, $G_M$}, {$I_F$, $G_F$}, {$G_M$, $G_F$}, {$I_M$}, {$I_F$}, {$G_M$}, {$G_F$}}.

Figure 4:
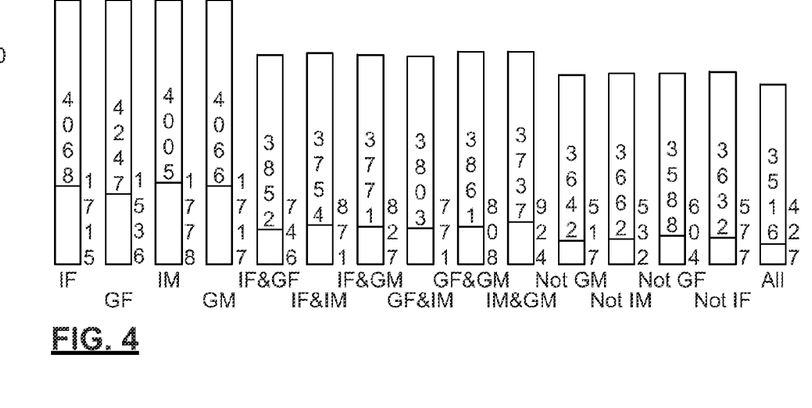
FIG. 4 is a graphic rendering of a number of genes that are conserved in a data series on a malaria experiment involving mice

FIG. 4 shows the set of genes with conserved expression trend across the entire set of experimental time points with constant disease state (top), in each sample, and in each combination of two or more samples, as well as the set of genes that do not stay constant but are affected similarly by the infection in the corresponding subset of samples (bottom). Among the 3943 probes conserved in the four biological samples {$I_M$, $I_F$, $G_M$, $G_F$}, 3516 genes are shown to be constant, whereas 427 have similar ranking patterns across all four samples.

Figure 5:
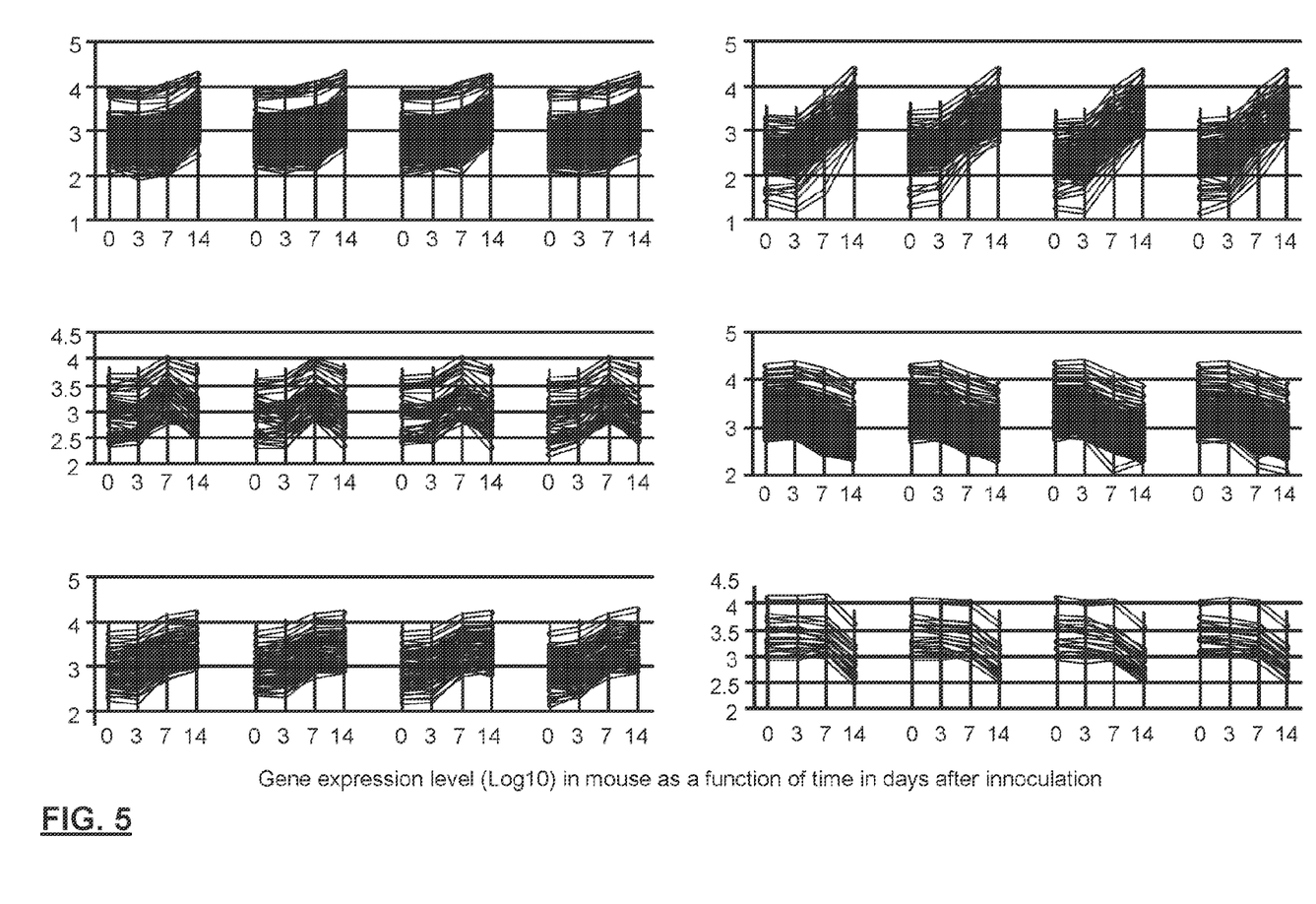
FIG. 5 illustrates specific value sequences in multiplots for each of 6 clusters of the example in FIG. 4, in each of 4 samples.
Figure 6:
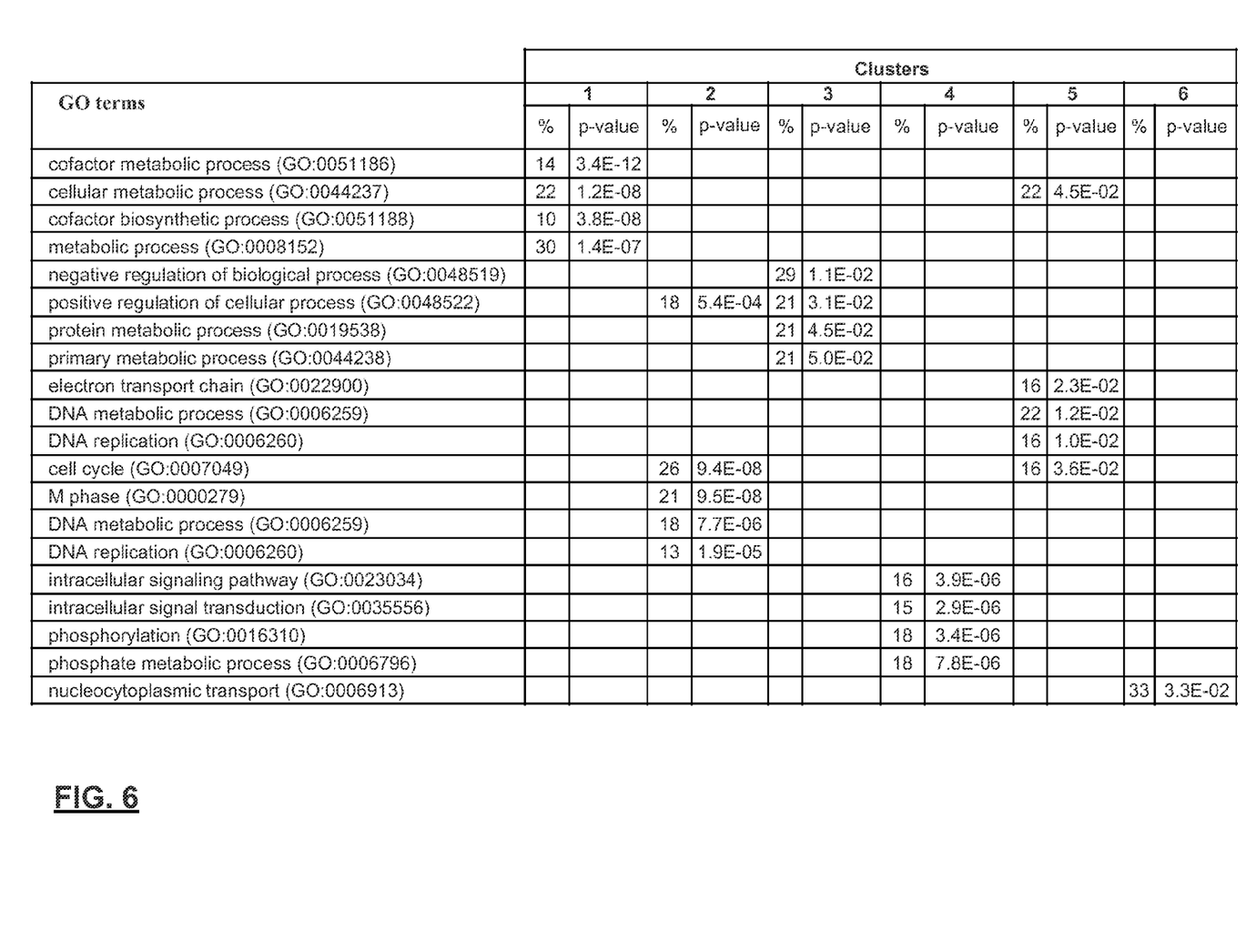
FIG. 6 is a table showing gene ontology analysis results.

These 427 genes are further clustered into 6 groups (FIG. 5). Clearly the genes in FIG. 5 have similar behaviour in the four samples and across the entire time series. Most of these genes may play a housekeeping role in this particular scenario. In other words, they represent the set of genes that are co-expressed regardless of the experimental condition to maintain basic cellular function. Indeed, Gene ontology analysis of these six clusters is shown in a table as FIG. 6. GOAL software [22] showed that the genes of FIG. 5 are involved in similar molecular function and biological processes, such as protein and DNA binding, transcription regulation, cell cycle and basic metabolism.

Figure 7:
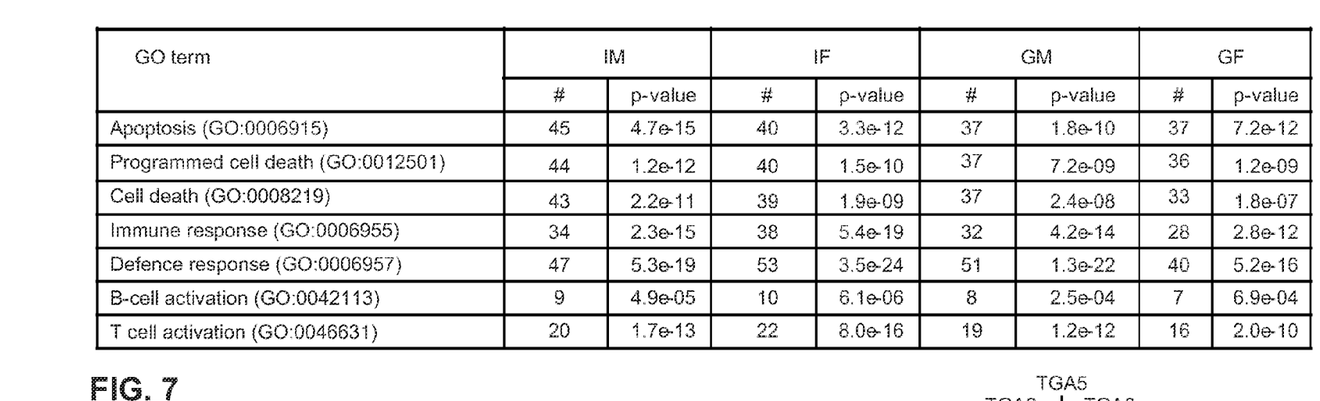
FIG. 7 is a table showing the gene ontology evaluation of the differences between samples in malaria experiment involving mice.

The results shown in FIG. 4 suggest that intact male ($I_M$) has the highest number of genes (1778) affected following pathogen attack, and lowest number of genes (4005) unaffected. This indicates that $I_M$ is probably more vulnerable to *P. chabaudi* infection compared to the other three phenotypes. This is consistent with the phenotypical observation made in [20], which suggested that intact males ($I_M$) were more likely to die than intact females ($I_F$) following *P. chabaudi* infection. Indeed gene ontology analysis shows that $I_M$ have more genes involved in the GO biological process terms like, cell death (GO:0008219), programmed cell death (GO:0012501), apoptosis (GO:0006915) than $I_F$ (FIG. 7). FIG. 7 illustrates the biological evaluation of the differences between $I_F$, $I_M$, $G_F$, and $G_M$. On the other hand, these same results showed that gonadectomy of male altered the sex-associated differences, suggesting that sex steroid hormone may modulate immune responses to infection [20].

In terms of differences between the four samples tested, our analysis identified genes that were unique to only one sample, and a combination of two and more samples. For example we identified 251, 266, 216, and 245 genes unique to $I_M$, $I_F$, $G_M$, and $G_F$ respectively. These genes may be the origin of the differences between the four samples after *P. chabaudi* infection. Thus, they may represent potential targets or biomarkers to be used not only to understand the differences between the samples, but also to develop novel therapeutic means.

Biological Application 2

The OPTricluster algorithm was applied to study similarities and differences in pathogen defence mechanism of *Arabidopsis thaliana*. The goal of the study was to understand the roles of NPR1 and some of TGA family transcription factors (TFs) during systemic acquired resistance in *A. thaliana*. The 3D microarray data used here was obtained using Affymetrix *Arabidopsis* Genechip consisting of 22,810 probes. The Columbia wild-type (W), mutant npr1 (P), double mutant tga1 tga4 ($Z_1$), and triple mutant tga2 tga5 tga6 ($Z_2$) were treated with salicylic acid (SA) for 0, 1, and 8 hours. After data pre-processing and normalization, 3945 significant genes were retained. We set the Columbia wild-type as our baseline and took the $\log_2$ ratio of the mutant gene expression levels over the wild-type at respective time points. The gene expression matrix was discretized into three numbers (−1, 0, and 1) for a given threshold 6=0.5, corresponding to down-regulation, constant, and up-regulation relative to the baseline (wild-type) respectively. Hence, we ended up with an N×M×L matrix, which had N=3945 rows (genes), M=3 columns (samples), and L=3 time points. This corresponds to the differential expression of the three mutant sets: npr1-3, tga1 tga4, and tga2 tga5 tga6 as compared to the wild type, across the three time points (0, 1, and 8 h).

Figure 8:
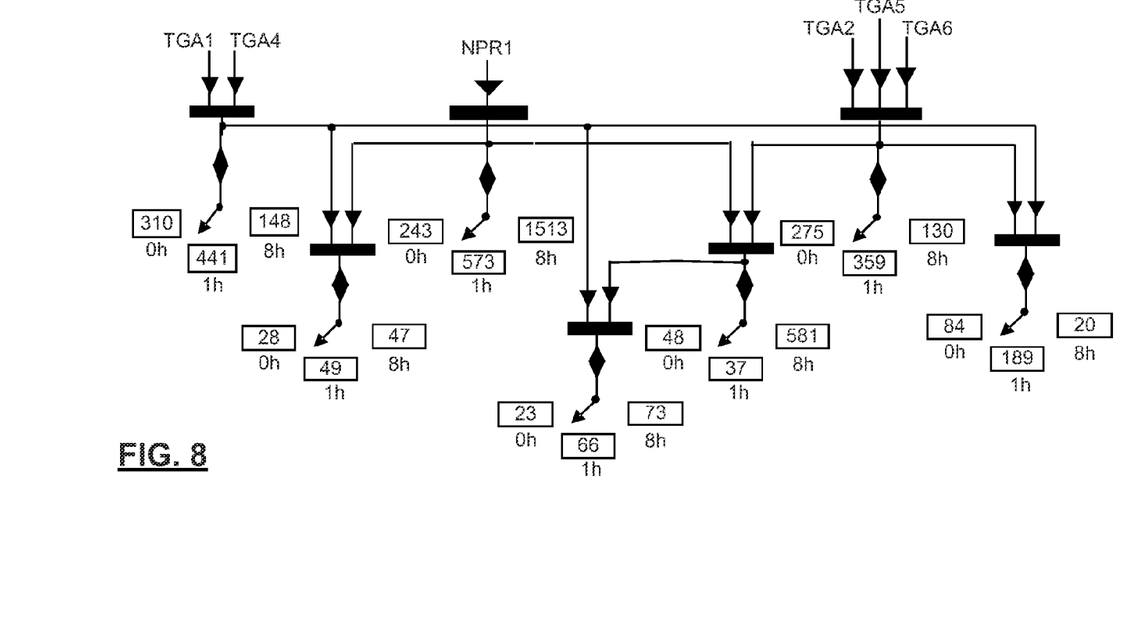
FIG. 8 is a wiring diagram showing a generic network presentation of the clustering algorithm.

With the N×M×L discretized gene expression matrix, the algorithm identified the set of genes that are controlled by the TFs at each time point, to study similarities and differences between them, and to infer a temporal transcriptional regulatory network controlling SAR in *A. thaliana*. OPTricluster generated $2^3-1$=7 subsets of samples ({P, $Z_1$, $Z_2$}, {P, $Z_1$}, {P, $Z_2$}, {$Z_1$, $Z_2$}, {P}, {$Z_1$}, {$Z_2$}). FIG. 8 shows a wiring diagram of the genetic network of SAR in *A. thaliana* at 0 h, 1 h, and 8 h inferred using the OPTricluster algorithm. For example, our analysis showed that only 23, 66, and 73 are either down- or up-regulated by the combined action of the three sets of TFs at 0, 1, and 8 h respectively. The number of NPR1 targeted genes is less than that of TGA1 TGA4 and TGA2 TGA5 TGA6 at 0 h. But at 8 h, it is the reverse situation where the number of NPR1 targeted genes is higher than those regulated by TGA1 TGA4 and TGA2 TGA5 TGA6, respectively. This is consistent with the fact that NPR1 gene expression in the Columbia wild type was initially moderate but drastically increased at 1 hour and increased further until 8 hours after SA treatment.

Gene ontology (GO) analysis using the GOAL software [22] reveals that several of the genes that are regulated by the three set of TFs (NPR1, TGA1 TGA4, and TGA2 TGA5 TGA6) at 8 h (FIG. 8) are annotated due to response to stimulus (GO:0050896; p-value=1.1e-08), stress (GO: 0006950; p-value=1.7e-05), abiotic stimulus (GO:0009628; p-value=3.1e-05), biotic stimulus (GO:0009607; p-value=1.3e-03), and defence mechanism (GO:0006952; p-value=5.0e-02). These correspond to the fact that the plants were treated by SA, which mimic pathogen infection. They also confirm the fact that the TFs tested in this study are known to play major roles in plant defence mechanism [17]. Another interesting observation is that a significant number of genes that stay constant across the three experimental time points are responsible for photosynthesis (GO:0015979; p-value=3.3e-25, and KEEG pathway ath00195 p-value=3.4e-10), which are not closely related with pathogen infection. These results confirmed that during pathogen attacks, the plant is mobilized for defence. In this application of OPTricluster, similarities in gene expression profiles of *A. thaliana* with single, double or triple mutations of key transcription factors in the defence signalling network were analyzed. The network dynamics over a time series was observed after treatment with salicylic acid (SA), which mimics a pathogen infection. Most SA-responsive genes were found to be affected by at least one mutation and that most affected genes fit one of a few patterns of regulation. OPTricluster provided a first glimpse into the temporal pattern of the gene regulatory network during systemic acquired resistance in *A. thaliana*.

In summary, analyses of well-defined *A. thaliana* short time-series 3D gene expression data, and immune responses in mice infected by malaria using OPTriciuster revealed significant biological patterns. The software has further been used to cluster Canola datasets, to identify sets of genes that are involved in seed developments, and fatty acid metabolisms, and has proven useful in these analyses.

The present invention provides a novel 3D clustering algorithm, especially useful in clustering multidimensional data analysis. The developed algorithm can be used to identify statistical and biological significant triclusters from a 3D gene expression data, to study similarities and differences in biological samples or related species in term of co-expression, co-regulation, and genetic pathways, and can be used as a preliminary tool to reconstruct dynamic regulatory maps, and gene regulatory networks. The novel triclustering algorithm according to the present invention described above can also be applied to extract useful information from several other data mining fields such as information retrieval and text mining, collaborative filtering, recommendation systems, target marketing and market research, and database research.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

REFERENCES

[1] Androulakis I. P., Yang E., and Almon R. R., "Analysis of Time-Series Gene Expression Data Methods, Challenges, and Opportunities," Annu. Rev. Biomed. Eng. 2007.9:205-228

[2] Bar-Joseph, Z., Gerber, G. K., Gifford, D. K., Jaakkola, T. S. and Simon, I. (2003) Continuous representations of time-series gene expression data. J Camput Biol, 10, 341-356.

[3] Schliep, A, Schonhuth, A and Steinhoff, C. (2003) Using hidden Markov models to analyze gene expression time course data. Bioinformatics, 19 Suppl1, i255-263.

[4] Yeung K., and Ruzzo W."An Empirical Study on Principal Component Analysis for Clustering Gene Expression Data, Bioinformatics, 17(9):763-774, 2001.

[5] Famili, F., Phan, S., Liu, Z., Pan, Y., Djebbari, A, Lenferink, A, O'Connor, M. "Discovering Informative Genes from Gene Expression Data: A Multi-Strategy Approach," The 18th European Conference on Machine Learning. Warsaw, Poland. Sep. 17-21, 2007. NRC 49839.

[6] Phan, S., Famili, F., Tang, Z., Pan, Y., Liu, Z., Ouyang, J., Lenferink, A, O'Connor, M. "A Novel Pattern Based Clustering Methodology for Time-Series Microarray Data," International Journal of Computer Mathematics. Volume 84, Number 5. May 2007. pp. 585-597. NRC 48820.

[7] Tang, Z., Phan, S., Pan, Y., Famili, F., "Prediction of Co-Regulated Gene Groups through Gene Ontology," Proceedings of the 2007 IEEE Symposium on Computational Intelligence in. Bioinformatics and Computational Biology (CICBC 2007). Honolulu, Hi., USA ISBN: 14244-0710-9. Apr. 1-5, 2007. pp 178-184. NRC 48806.

[8] Madeira S. C. and Oliveira A. L., "Biclustering algorithms for biological data analysis: a survey," IEEE Transactions on Computational Biology and Bioinformatics, vol. 1, no. 1, pp. 24-45, 2004.

[9] A H. Tewfik A H., TChagang A. B., and Vertatschitsch L., "Parallel identification of gene biclusters with coherent evolution," IEEE Transactions on Signal Processing, vol. 54, no. 6, pp. 2408-2417, 2006, Special issue on Genomics Signal Processing.

[10] Tchagang A B. and Tewfik A. H., "DNA Microarray Data Analysis: A Novel Biclustering Algorithm Approach," EURASIP Journal on Applied Signal Processing, vol. 2006, Article ID 59809, 12 pages, 2006. doi:10.1155/ASP/2006/59809

[11] Prelic A., Bleuler S., Zimmermann P., Wille A, Buhlmann P., Gruissem W., Hennig L., Thiele L., and Zitzler E., A systematic comparison and evaluation of biclustering methods for gene expression data, Bioinformatics, 22 (2006), pp. 1122-9.

[12] Ben-Dor A, Chor B., Karp R., and Yakhini Z., "Discovering local structure in gene expression data: the order-preserving submatrix problem," in Proceedings of the 6th Annual International Conference on Computational Biology (RECOMB '02), pp. 49-57,Washington, D.C., USA, April 2002

[13] Jiang D., Pei J., Ramanathany M., Tang C. and Zhang A, Mining coherent gene clusters from gene-sample-time microarray data. In Proc. of the 10th ACM SIGKDD Conference (KDD'04), 2004

[14] Zhao L. and Zaki M. J., TRICLUSTER: An effective algorithm for mining coherent clusters in 3D microarray Data. In Proc. of SIGMOD'05.

[15] Araujo R., Trielli G., Orair G., Meira Jr. W., Ferreira R., and Guedes D. "ParTriCluster: A Scalable Parallel Algorithm for Gene Expression Analysis" Proceedings of the 18th International Symposium on Computer Architecture and High Performance Computing (SBAC-PAD'06)

[16] Jiang H., Zhou S., Guan J., and Zheng Y., "gTRICLUSTER: A More General and Effective 3D Clustering Algorithm for Gene Sample-Time Microarray Data BioDM 2006, LNBI 3916, pp. 48-59, 2006. Springer-Verlag Berlin Heidelberg 2006.

[17] Eulgem T., " Regulation of the Arabidopsis Defense Transcriptome," TRENDS in Plant Science, Vol. 1 0 No. 2 Feb. 2005

[18] Pieterse C. M. J., and Van Loon L. C., "NPR1: the spider in the web of induced resistance signaling pathways," Current Opinion in Plant Biology 2004, 7:456-464

[19] Johnson C., Boden E., and Arias J., Salicylic Acid and NPR1 Induce the Recruitment of transActivating TGA Factors to a Defense Gene Promoter in Arabidopsis," The Plant Cell, Vol. 15, 1846-1858, August 2003.

[20] Cernetich A, Garver L S, Jedlicka A E, Klein P W, Kumar N, Scott A L, Klein S L: Involvement of gonadal steroids and gamma interferon in sex differences in response to blood-stage malaria infection. *Infect Immun.* 2006, 74(6): 3190-203.

[21] GEO Database [http://www.ncbi.nlm.nih.gov/geo/]

[22] Tchagang A B, Gawronski A, Bérubé H, Phan S, Famili F, Pan Y: GOAL: A Software Tool for Assessing Biological Significance of Genes group. *BMC Bioinformatics* 2010, 11:229.

What is claimed is:

1. A data clustering method performed with an electronic processor comprising:
   providing access to a dataset stored electronically in a dataset structure on a memory, the dataset having at least a few thousand aligned sequences in at least one set, each sequence having exactly B values, where $3 \leq B \leq 20$, the value sequences representing changes in observed values as a function of a variable subject to noise;
   computing an order preserving abbreviated characterization of each of the value sequences, such that two value sequences will only have the same abbreviated characterization if they exhibit equivalent trends under any sequence reordering; and
   associating value sequences characterized the same to respective clusters by annotating a record containing the value sequence to identify the characterization, and/or by adding an identifier of the associated value sequence to a record created for the class.

2. The method of claim 1 wherein access is provided to a dataset in a form of a three-dimensional array of values with the first dimension being associated with a set of parameters, and the second dimension being associated with a set of elements, where each of the value sequences represents the function of the variable associated with a given parameter under a given element.

3. The method of claim 2 further comprising:
   regrouping a collection of associated parameters, each from a respective set of the sequences, and identifying a set of elements, over which the collection of associated parameters are clustered;
   regrouping a collection of nominally associated parameters, each from a respective set of the sequences, and identifying a set of elements, over which the nominal parameter is clustered;
   regrouping two or more collections of associated parameters, each collection having one parameter from each set of the sequences that are associated, and identifying the two or more collections of associated parameters are respectively clustered throughout all sets;
   regrouping two or more collections of nominally associated parameters, each parameter having one value sequence in each set of the sequences, and identifying a set of elements over which the two or more nominal parameters are respectively clustered;
   regrouping two or more collections of associated parameters, each collection having one parameter from each set of the sequences that are associated, and identifying a set of elements over which the two or more collections of associated parameters are co-clustered;
   regrouping two or more collections of nominally associated parameters, each parameter having one value sequence in each set of the sequences, and identifying a set of elements over which the two or more nominal parameters are co-clustered;
   regrouping two or more collections of associated parameters, each collection having one parameter from each set of the sequences that are associated, and identifying a set of elements, over which the two or more collections of associated parameters are clustered respectively in associated clusters; or
   regrouping two or more collections of nominally associated parameters, each parameter having one value sequence in each set of the sequences, and identifying a set of elements over which the two or more nominal parameters are clustered respectively in associated clusters.

4. The method of claim 2 wherein associating value sequences characterized the same comprises receiving identification of one or more of the sets, and associating all value sequences characterized the same within the identified sets.

5. The method of claim 2 wherein access is provided to a dataset in a form of a three-dimensional array of values with the first dimension being associated with a set of constituents, and the second dimension being associated with a set of samples, where each of the value sequences represents the concentration of a given constituent within the given sample as a function of the variable.

6. The method of claim 2 wherein access is provided to a dataset in a form of a three-dimensional array of values with the first dimension being associated with a set of constituents, and the second dimension being associated with a set of samples, where each of the value sequences represents the concentration of a given constituent within the given sample as a function of time.

7. The method of claim 6 further comprising identifying constituents that have order preserving concentrations over some but not all of the samples.

8. The method of claim 2 wherein access is provided to a dataset in a form of a three-dimensional array of values with the first dimension being associated with a set of genes, and the second dimension being associated with a set of samples, where each of the value sequences represents the concentration of a given gene within the given sample as a function of time.

9. The method of claim 1 wherein computing the order preserving characterization comprises generating a rank sequence in which each of the values in the sequence is replaced with its corresponding rank in the sequence, in either an increasing order or a decreasing order.

10. The method of claim 1:
    wherein access is provided to a dataset in which the sequences of B values are extracted from respective longer value sequences;
    further comprising iterating the computation of the order preserving abbreviated characterization for each of a plurality of the extracted sequences of B values; and
    wherein associating value sequences characterized the same to respective clusters comprises associating two of the longer value sequences with a respective cluster if corresponding ones of the plurality of extracted sequences of B values of the two longer value sequences match.

11. The method of claim 1 further comprising performing statistical significance analysis on each said identified order preserving clusters.

12. The method of claim 11 wherein performing statistical significant analysis further comprises computing a tail probability that a random data set will contain an order preserving cluster.

13. The method of claim 1 further comprising pre-processing all of the values through data smoothing and quantification, prior to computing the order preserving characterization.

14. The method of claim 1 further comprising performing a biological evaluation of each of the identified order preserving clusters, by computing a Fisher's exact test on a 2×2 contingency table to produce a plurality of values corresponding to a significance of gene ontology enrichment in a given order preserving cluster.

15. A computer program product comprising a non-transitory computer-readable storage medium storing a comprising computer program instructions that, when executed by a processor, implement the method of clustering data analysis of claim 1.

16. A system for analysing data, the system comprising:
a memory for storing a dataset structure containing an electronically accessible dataset, the dataset having at least one set of S aligned sequences of B values, where the value sequences represent changes in observed values as a function of a variable subject to noise, and $3 \leq B \leq 20$;
an electronic processor configured to access the dataset, having program instructions for:
computing an order preserving abbreviated characterization of each of the value sequences, such that two value sequences will have the same abbreviated characterization only if they exhibit equivalent trends under any sequence reordering; and
associating value sequences characterized the same to respective clusters by annotating a record containing the value sequence to identify the characterization, and/or by adding an identifier of the associated value sequence to a record created for the class.

17. The system of claim 16 wherein the dataset is in a form of a 3D array of values with a first dimension associated with a set of parameters, a second dimension is associated with a set of elements, and the value sequences representing an observed value associated with a said parameters under a given element.

18. The system of claim 16 wherein the electronic processor is configured to operate a series of modules, including:
a ranking module adapted to rank all of the measurement values across a third dimension of the array in a selected one of an increasing order or a decreasing order and producing a 3D array of ranked. values therefrom;
a pattern identification module adapted to identify coherent 3D patterns in the 3D array of ranked values and counting the number of identified coherent 3D patterns; and
an assignment module adapted to, for each said identified coherent three dimensional pattern, assign parameters with a similar ranking along the third dimension and across subsets of the set of elements to a same group, thereby identifying order preserving triclusters.

19. A data clustering method performed with an electronic processor comprising:
providing access to an experimental genomic, proteomic, or materiomic dataset stored electronically in a dataset structure on a memory, the dataset having at least a few thousand aligned short time series sequences, each sequence associated with a respective sample, and a respective gene, protein, or material component, and comprised of a sequence of 3 to 20 values, each of the values in the sequence representing an observed measurement of the associated component within the associated sample at a respective experimental condition associated with the position of the value in the sequence;
computing an order preserving abbreviated characterization of each of the value sequences, such that two value sequences will only have the same characterization if they exhibit equivalent trends under any sequence reordering; and
associating value sequences characterized the same to respective clusters by annotating a record containing the value sequence to identify the characterization, and/or by adding an identifier of the associated value sequence, component, sample or experimental condition to a record created for the class.

* * * * *